United States Patent
Corbin et al.

(10) Patent No.: US 9,921,184 B2
(45) Date of Patent: Mar. 20, 2018

(54) SODIUM-CESIUM IONIZATION DETECTOR

(71) Applicant: TerraPower, LLC, Bellevue, WA (US)

(72) Inventors: Robert Alan Corbin, North Bend, WA (US); David Nash, Bellevue, WA (US); Christopher M. Regan, Seattle, WA (US); Shane Schweiger, Bellevue, WA (US); Randy Thompson, Bellevue, WA (US); Jacob Wilcox, Kirkland, WA (US)

(73) Assignee: TerraPower, LLC, Bellevue ( * ) Notice: Subject to any disclaimer, the term of this patent is extended or adjusted under 35 U.S.C. 154(b) by 0 days.

(21) Appl. No.: 15/492,813

(22) Filed: Apr. 20, 2017

(65) Prior Publication Data
US 2017/0336358 A1 Nov. 23, 2017

Related U.S. Application Data

(60) Provisional application No. 62/339,221, filed on May 20, 2016.

(51) Int. Cl.
*G01N 27/62* (2006.01)
*G01N 33/00* (2006.01)
*G21C 17/025* (2006.01)

(52) U.S. Cl.
CPC ........ *G01N 27/626* (2013.01); *G01N 33/0036* (2013.01); *G21C 17/025* (2013.01)

(58) Field of Classification Search
CPC . G01N 27/626; G01N 33/0036; G21C 17/025
See application file for complete search history.

(56) References Cited

U.S. PATENT DOCUMENTS

| | | | |
|---|---|---|---|
| 4,047,040 A * | 9/1977 | Houston | H01J 47/02 250/385.1 |
| 4,047,101 A | 9/1977 | Bauerle | |
| 4,095,171 A | 6/1978 | Baurle | |
| 4,117,396 A | 9/1978 | Berkey | |
| 4,121,458 A * | 10/1978 | Fort | H01J 41/08 250/382 |
| 4,325,029 A | 4/1982 | Hrizo | |
| 4,366,438 A | 12/1982 | Ibe | |
| 4,782,235 A * | 11/1988 | Lejeune | H01J 27/18 250/423 R |
| 4,845,364 A * | 7/1989 | Alexander | H01J 49/142 250/288 |

(Continued)

OTHER PUBLICATIONS

Breitwieser et al., Saha-Langmuir Surface Ionizaiton Relation, Thermionic Conversion Specialist Conference sponsored by the Institute of Electrical and Electronics Engineers, San Diego, CA Oct. 25-27, 1965.

(Continued)

*Primary Examiner* — Marcus Taningco

(57) ABSTRACT

Sodium-cesium detection systems and methods for the simultaneous detection of both sodium (Na) and cesium (Cs) in gas are provided. The detection systems include two non-identical ionization chambers each having an anode and a cathode that ionize Na and Cs in gas. Each ionization chamber generates a current proportional to the Na and Cs concentration and based on the current, Na concentration and Cs concentration in the gas is determined.

21 Claims, 7 Drawing Sheets

(56) References Cited

U.S. PATENT DOCUMENTS

| | | | | |
|---|---|---|---|---|
| 6,316,773 | B1* | 11/2001 | Giakos | G01T 1/2935 |
| | | | | 250/370.01 |
| 6,840,085 | B1* | 1/2005 | Kolaja | G01N 30/7206 |
| | | | | 250/374 |
| 8,421,470 | B2* | 4/2013 | Kitano | G01N 27/68 |
| | | | | 324/464 |
| 8,502,158 | B1* | 8/2013 | Gordeev | G01T 7/00 |
| | | | | 250/394 |
| 9,341,596 | B1* | 5/2016 | Chen | G01N 27/66 |
| 2016/0320334 | A1* | 11/2016 | Nakatou | G01N 27/409 |

OTHER PUBLICATIONS

Dunn et al., Calculation of Electrical and Thermal Conductivities of Metallurgical Plasmas, Bulletin (Welding Research council (U.S.)), 357, 21 pages, 1990.

Hrizo et al., Sodium Ionization Detector and Sensor, Final Technical Report, Westinghouse Research and Development Center, Contract EN-77-C-02-4197.A000 Department of Energy, May 8, 1979.

J. Lau, Electrical Conductivity of Inert Gases—Seed Combination in Shock Tubes, Defesnse Documentation Center for Scientific and Technical Information, DDC No. 445232, Aug. 1964.

K. Swaminathan, Development of a Sodium Ionisation Detector for Socium-to-gas Leaks, Reactor Reasearch Centre, Kalpakkam 603 102 Tamil Nadu, India, 1979.

Langmuir et al., Thermionic Effects Caused by Vapours of Alkali Metals, Proc. of the Royal Society A Mathematical Physical & Engineering Sciences, 107, doi: 10.1098/rspa.1025.0005, published Jan. 1, 1925.

Morris et al., An Evaluation of Liquid Metal Leak Detection Methods for the Clinch River Breeder Reactor Plant, Prepared for the US Nuclear Regulatory Commission under Related Services Contract 8D08 to the Prime Contract CY-76-C-06-1830 with the Department of Energy, Dec. 1977.

Mozgovoy et al., New Equations of State and the Tables of Cesium Vapor Thermodynamic Properties at Termperatures <1700K and Pressure <5.5 Mpa, Chemistry and Computational Simulation. Butlerov Communications. vol. 3. No. 10, pp. 36-38, 2001.

Sodium Cesium Ion Detector—Lab Poster, shown at Open House, Nov. 20, 2015.

Sylvia et al., Development of sodium leak detectors for PFBR, Nuclear Engineering and Design 249 (2012) 419-431.

Sylvia et al., Sensors in Sodium Cooled Fast Breeder Reactors, National Journal of Electronic Sciences and Systems, vol. 3, No. 2, Oct. 2012.

Vaidyanathan et al., Sensors in Sodum Cooled Fast Breeder Reactors, National Journal of Electronic Sciences & Systems, vol. 3 No. 2, Oct. 2012.

Wolson et al., Development of on-line Monitoring Device to Detect the Presence/Absence of Sodium Vapor, ANL—83-21, Mar. 1983.

Yamamoto et al., Development of Fluctuation Monitor Type Sodium Ionization Detector, Journal of Nuclear Science and Technology, 23:7, 573-581, 1986.

Yamamoto et al., Using Anemometer for Particle Size Measurement of Sodium Mist, Journal of Nuclear Science and Technology, 16:8, 616-618, 1979.

* cited by examiner

SODIUM-CESIUM IONIZATION DETECTOR

RELATED APPLICATIONS

This application claims the benefit of U.S. Provisional Application No. 62/339,221, filed May 20, 2016, entitled "Sodium-Cesium Ionization Detector," which is hereby incorporated by reference.

INTRODUCTION

Sodium-cooled nuclear reactors have been operated and studied in the past for their suitability for use in electricity generating nuclear power plants. One drawback identified during the operation of the research reactors was the carry-over of Cs-137, a fission product, out of the liquid sodium coolant and into the vapor treatment system of the reactor. In most previous reactor designs, the consequences of cesium release were relatively small because the quantity released from a few failed fuel pins was small. However, since some modern reactors, such as Traveling Wave Reactors, currently under development are designed to operate with vented fuel pins, the quantity of cesium released to the primary sodium coolant and reactor cover gas space will be much greater.

Sodium-Cesium Ionization Detector

This disclosure describes new sodium-cesium detection systems and methods for the simultaneous detection of both sodium (Na) and cesium (Cs) in gas. The new detection systems include two non-identical ionization chambers each having an anode and a cathode that ionize Na and Cs in gas. Each ionization chamber generates a current proportional to the Na and Cs concentration and based on the current, Na concentration and Cs concentration in the gas is determined.

These and various other features as well as advantages which characterize the sodium-cesium detection systems and methods described herein will be apparent from a reading of the following detailed description and a review of the associated drawings. Additional features are set forth in the description which follows, and in part will be apparent from the description, or may be learned by practice of the technology. The benefits and features of the technology will be realized and attained by the structure particularly pointed out in the written description and claims hereof as well as the appended drawings.

It is to be understood that both the foregoing introduction and the following detailed description are exemplary and explanatory and are intended to provide further explanation of the invention as claimed.

BRIEF DESCRIPTION OF THE DRAWINGS

The following drawing figures, which form a part of this application, are illustrative of described technology and are not meant to limit the scope of the invention as claimed in any manner, which scope shall be based on the claims appended hereto.

DETAILED DESCRIPTION

Before the sodium-cesium detection systems and methods that are the subject of this disclosure are described, it is to be understood that this disclosure is not limited to the particular structures, process steps, or materials disclosed herein, but is extended to equivalents thereof as would be recognized by those ordinarily skilled in the relevant arts. It should also be understood that terminology employed herein is used for the purpose of describing particular embodiments only and is not intended to be limiting. It must be noted that, as used in this specification, the singular forms "a," "an," and "the" include plural referents unless the context clearly dictates otherwise. Thus, for example, reference to "a lithium hydroxide" is not to be taken as quantitatively or source limiting, reference to "a step" may include multiple steps, reference to "producing" or "products" of a reaction should not be taken to be all of the products of a reaction, and reference to "reacting" may include reference to one or more of such reaction steps. As such, the step of reacting can include multiple or repeated reaction of similar materials to produce identified reaction products.

This disclosure describes systems and methods for the simultaneous detection of both Na and Cs in gas. For the purposes of this application, embodiments of a Na—Cs detector will be described in the context of a sodium-cooled nuclear reactor in which the detection of Cs in carryover gas is important. However, it will be understood that the detection systems and methods may be adapted for use in any context in which Cs needs to be detected when Na is also present, not just in nuclear reactor contexts.

Figure 1:
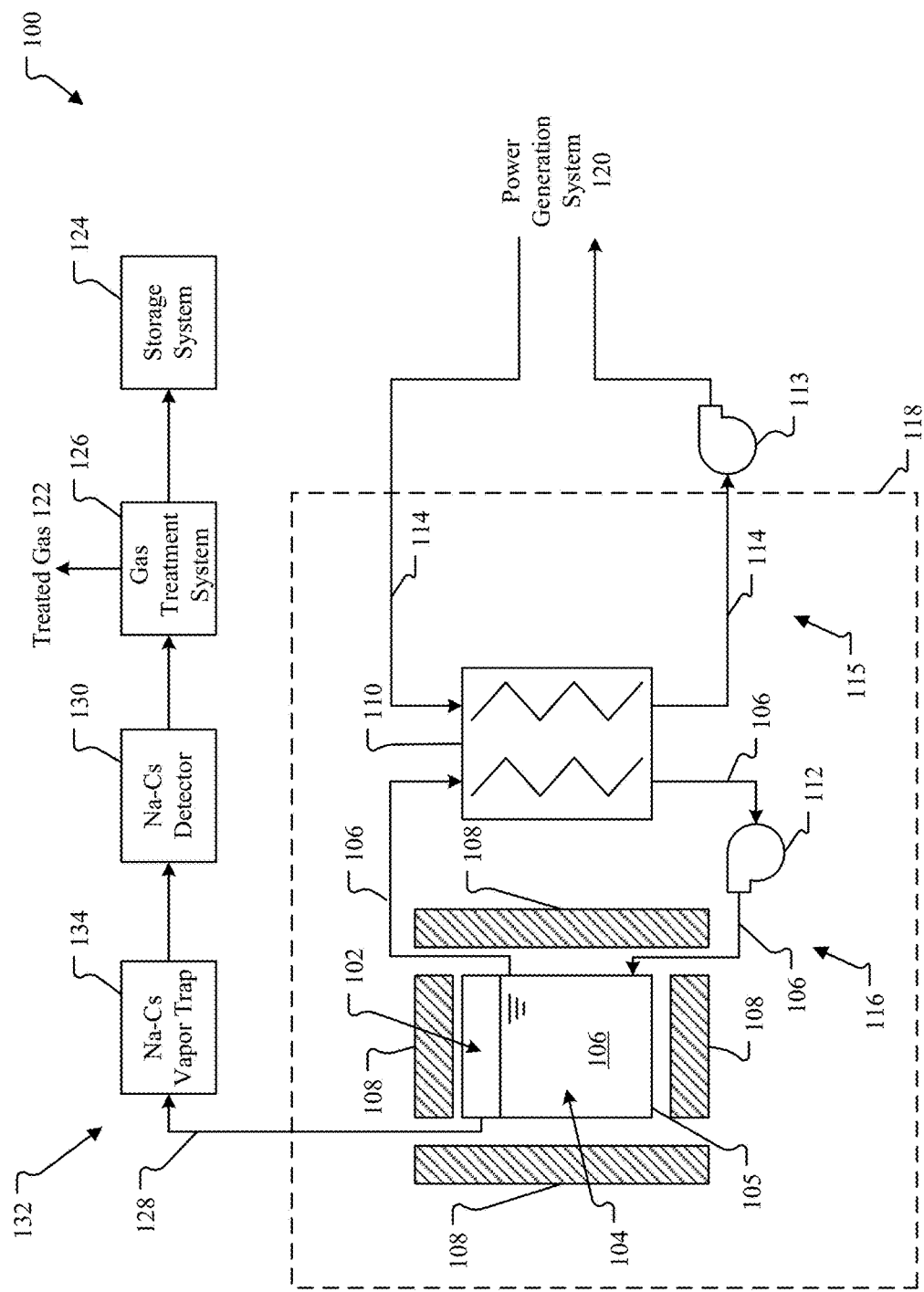
FIG. 1 illustrates, in a block diagram form, some of the basic components of a sodium-cooled nuclear reactor.

FIG. 1 illustrates, in a block diagram form, some of the basic components of a sodium-cooled nuclear reactor. In general, a reactor 100 includes a reactor core 104 in a reactor vessel 105, the core 104 containing a fissionable fuel that generates heat which is removed via a liquid coolant 106, such as sodium metal. For the purposes of this disclosure, fissionable material includes any fissile material, any fertile material or combination of fissile and fertile materials and the coolant 106 is sodium metal. The fissionable fuel may be in solid or liquid form (at operating temperatures) and may or may not be held within some container. In a molten fuel embodiment (not shown), the coolant 106 may be a mixture of uranium and sodium salts in which the mixture is both the primary coolant and the fuel. In a solid fuel embodiment, the fuel may be a solid uranium compound held within one or more containers that are contacted by, or submerged in a pool of, sodium metal coolant.

In any case, the fissionable fuel transfers heat to a primary liquid coolant 106. The coolant 106 may be sodium metal. The coolant 106 may or may not completely fill the vessel 105 that contains the fuel, and the embodiment shown is illustrated with an optional headspace 102, which may be filled with an inert gas such as argon, above the level of the coolant 106. The size of the reactor core 104 is selected based on the characteristics and type of the particular fuel being used in order to achieve and maintain the fuel in an ongoing state of criticality, during which the heat generated by the ongoing production of neutrons in the fuel causes the temperature of the fuel to rise. The performance of the reactor 100 is improved by providing one or more reflectors 108 around the core 104 to reflect neutrons back into the core. The coolant 106 is circulated between the reactor core 104 and one or more primary heat exchangers 110 located outside of the core 104. The circulation may be performed using one or more pumps 112.

The primary heat exchangers 110 transfer heat from the coolant 106 to a secondary coolant 114 that is circulated through a secondary coolant loop 115. In an embodiment the secondary coolant may be sodium or another liquid metal such as lead, or a salt, such as $NaCl$—$MgCl_2$. In an embodiment, a reflector 108 is between each primary heat exchanger 110 and the reactor core 104 as shown in FIG. 1.

In the embodiment shown, a heated secondary coolant 114 from the primary heat exchangers 110 is passed to a power generation system 120 for the generation of some form of power, e.g., thermal, electrical or mechanical. The reactor core 104, primary heat exchangers 110, pumps 112, sodium coolant circulation piping (including other ancillary components that are not shown such as check valves, shutoff valves, flanges, drain tanks, etc.) and any other components through which the coolant circulates or contacts during operation can be referred to as the primary sodium coolant loop 116. Likewise, the secondary coolant loop 115 includes those components through which secondary coolant circulates, including the primary heat exchangers 110, coolant pumps 113, and secondary coolant circulation piping (including other ancillary components that are not shown such as check valves, shutoff valves, flanges, drain tanks, etc.).

The reactor 100 further includes at least one containment vessel 118 that contains the fuel and other radioactive material to prevent their release in case of an emergency. In a liquid fuel embodiment (as shown), the vessel will surround the primary sodium coolant loop 116 as the coolant is also the fuel. In a solid fuel embodiment, the solid fuel will be contained by the vessel 118 but not all of the sodium coolant loop 116 need be so contained. Note that, depending on the embodiment some or none of the secondary coolant loop 115 need be within the containment vessel 118.

FIG. 1 further discloses a carryover gas handling system 132. The handling system 132 receives carryover gas 128 and treats it for safe discharge to the atmosphere. The handling system 132 includes a gas treatment system 126, a Na—Cs detector 130, and a storage system for storing collected contaminants 124. The handling system 132 may receive carryover gas 128 from the headspace 102, as shown, and/or from any location in the coolant loop 116. The carryover gas 128, which may primarily be an inert gas such as argon, will contain some Na vapor as well as volatile fission products including Cs-137 and various isotopes of Kr, Xe, and Ar. The carryover gas 128 is then passed through a Na—Cs vapor trap 134 to remove Na and Cs from the carryover gas 128. Both Na and Cs will interfere with the operation of the downstream treatment systems, so the gas exiting the vapor trap 134 is monitored by the Na—Cs detector 130 to determine the amount of Cs in the carryover gas 128. The carryover gas stream then is passed to the gas treatment system 126 that removes or provides sufficient residence time for the decay of any other contaminants in the carryover gas. The cleaned gas 122 is then discharged to the atmosphere or recycled to some part of the power plant. Collected contaminants are kept in a storage system 124 for subsequent disposal.

In the embodiment illustrated in FIG. 1, the carryover gas 128 will include both Na and Cs vapor. As mentioned above, both Na and Cs are detrimental to the operation of gas treatment system 126, but not to the same extent. For example, the acceptable concentration of Cs in carryover gas output from the vapor trap may be less than 1 parts per million (ppm) by weight, which may be small when compared to the acceptable concentration of Na. Unless otherwise stated, all concentrations presented in ppm will be by weight. Therefore, it is helpful to independently monitor both how much Na and how much Cs is exiting the vapor trap in order to prevent damage to the downstream treatment systems. However, Na and Cs are both alkali metals and can be difficult to differentiate during monitoring.

Figure 2:
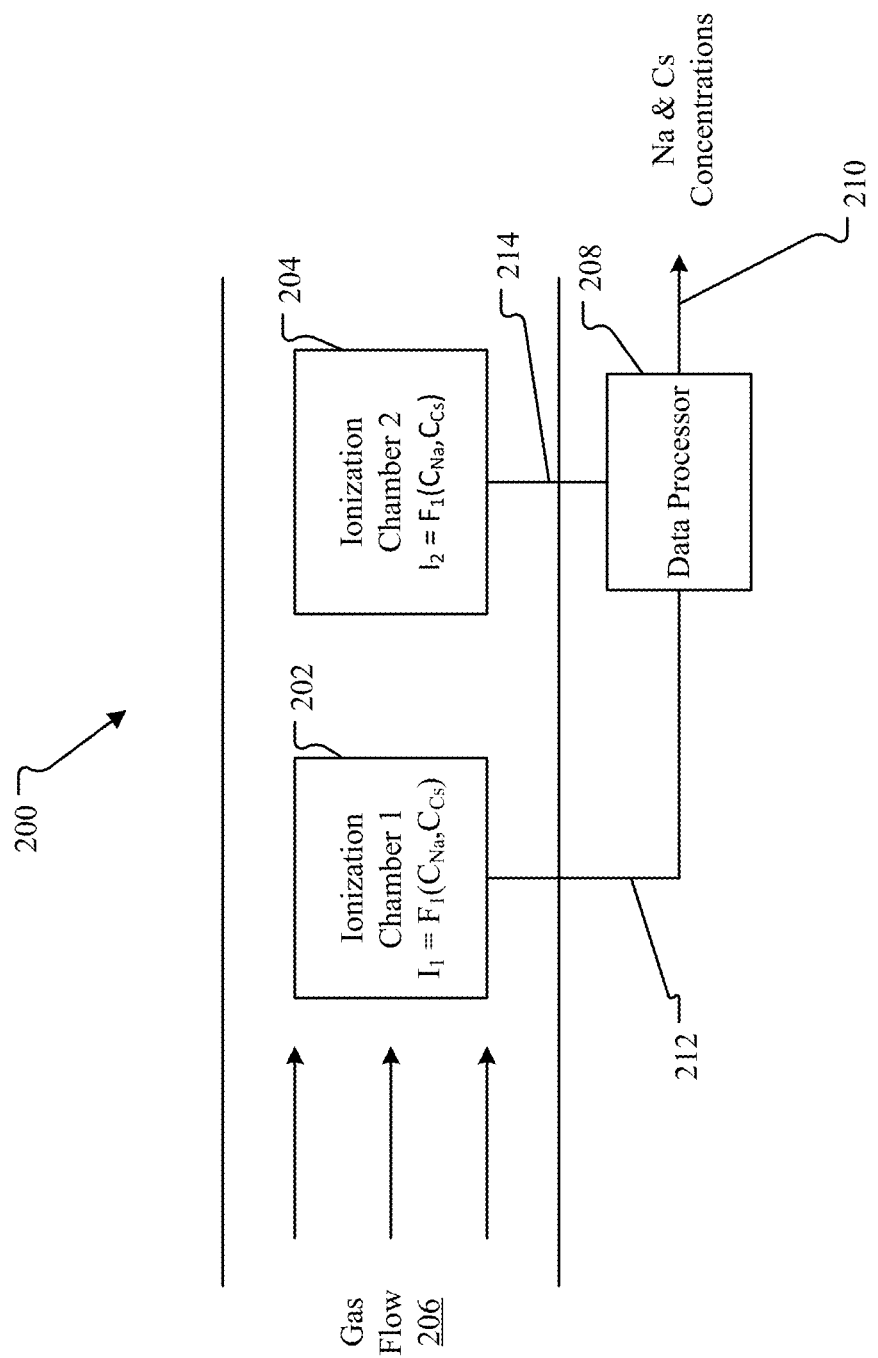
FIG. 2 illustrates an embodiment of a Na—Cs detector.

FIG. 2 illustrates an embodiment of a Na—Cs detector. In the detector 200, a pair of ionization chambers 202, 204 is used to monitor the gas, such as the gas discharged from the Na—Cs vapor trap. The ionization chambers 202, 204 may be in series (as illustrated) relative to the gas stream 206 to be monitored or in parallel (not shown). In an embodiment, the ionization chambers 202, 204 are instruments that use a hot wire to ionize atoms of Na and Cs in the gas and then monitor the resulting ionization current between an anode (which is also the hot wire) and cathode exposed to the gas.

The ionization chambers 202, 204 are not identical. Both ionize Na and Cs in the gas and generate a current proportional to Na and Cs concentration, but they react differently in that the proportionality is different between the chambers. In the embodiment shown in FIG. 2, the current output ($I_1$) 212 of the first chamber 202 is:

$$I_1 = I_{Na,1} + I_{Cs,1} \quad (1)$$

and the output ($I_2$) 214 of the second chamber 204 is:

$$I_2 = I_{Na,2} + I_{Cs,2} \quad (2)$$

In addition, the current output ($I_1$) 212 of the first chamber 202 is some function $F_1(C_{Na}, C_{Cs})$ of the Na concentration ($C_{Na}$) and Cs concentration ($C_{Cs}$). Likewise, the current output ($I_2$) 214 of the second chamber 204 is some function $F_2(C_{Na}, C_{Cs})$ of the Na and Cs concentrations. The two functions, $F_1$ and $F_2$, are different (that is, the functions can be represented by mathematically consistent equations and not variations of the same function, e.g., $F_1 \neq k \cdot F_2$ where k is a constant). The two functions, $F_1$ and $F_2$, are fixed by the design of the ionization chambers and can be determined by testing the ionization chambers under controlled conditions using known Na and Cs gas concentrations.

The fact that the two chambers 202, 204 output currents 212, 214 that are different functions of the same Na—Cs gas concentration allows the currents to be compared and the concentration of the each constituent to be determined by mathematical analysis. In the embodiment shown, the current outputs 212, 214 from the chambers 202, 204 are communicated to a data processor 208 that calculates and outputs 210 the concentrations of Na and Cs. An example calculation is provided below with reference to the specific embodiment of FIG. 3.

An output of the detector 200 is the concentrations of the analytes, in this embodiment Cs and Na. The concentrations may be displayed and/or stored as a part of ongoing monitoring or may be used by a safety system to either generate alarms or automatic shutdown signals upon detection of high concentrations of either Na or Cs in the gas leaving the vapor trap. For example, in an embodiment one or more Na thresholds and Cs thresholds may be compared in real time to the output 210 of the data processor. Upon determining that a concentration meets or exceeds a particular threshold, an action associated with the particular threshold (e.g., generate an alarm, send a message, issue a shutdown command, etc.) may be performed.

An aspect of this disclosure is how the different functions, $F_1$ and $F_2$, are created. In general, how the chamber designs are varied to create the different functions is irrelevant as long as the functions are fixed and different. Such different functions may be created by varying anode or cathode materials or coatings between chambers.

Another way of creating two ionization chambers having different functions, $F_1$ and $F_2$, for the same analytes has been found: varying the geometry of the anode or cathode between the chambers. It has been determined that different anode or cathode geometries, e.g., the first chamber utilizes a straight wire for a combination hot wire/anode and the second chamber utilizes a coiled wire for the hot wire/anode, result in different functions, $F_1$ and $F_2$.

Moreover, in the embodiment, the analytes have different sizes. That is, Cs has a larger atomic radius than Na. Since the analytes are different in size, the analytes react sufficiently different within the ionization chamber to create the functions, $F_1$ and $F_2$, which are not a variation of the same function as described above.

Figure 3:
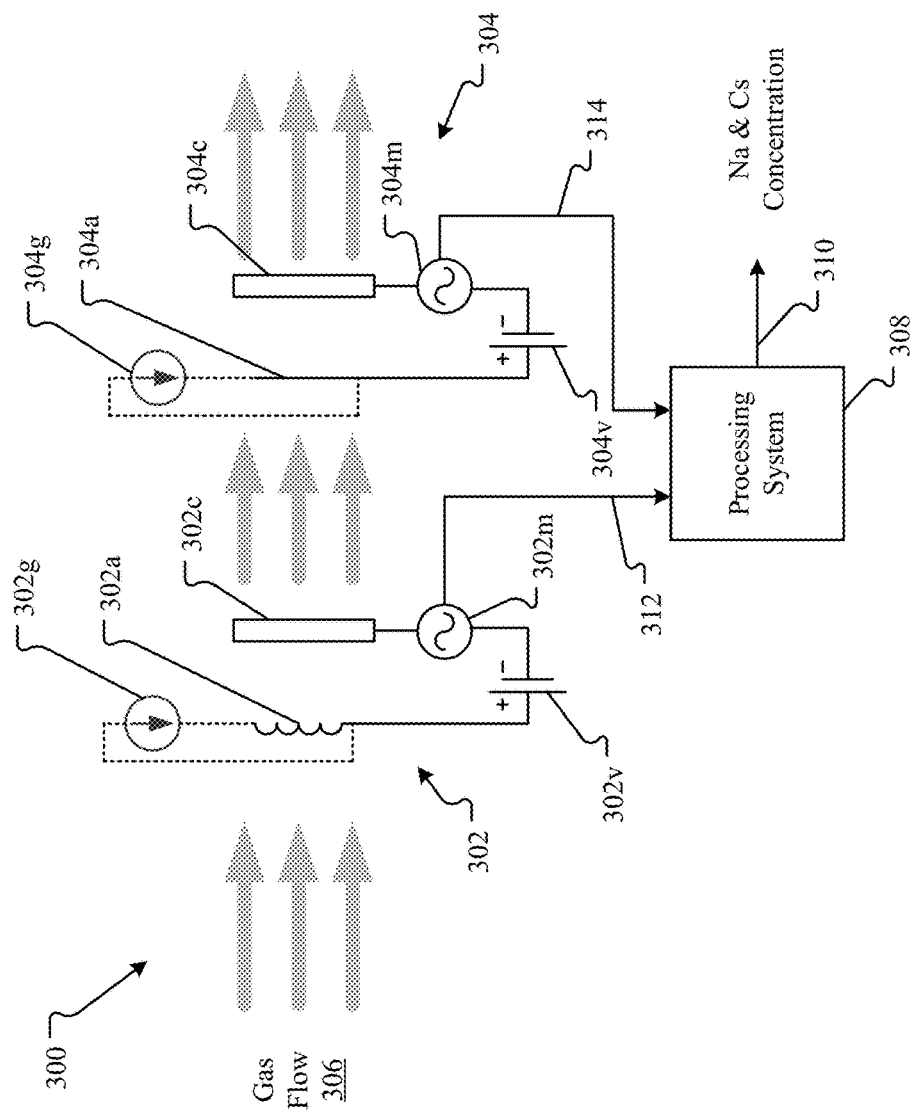
FIG. 3 illustrates an embodiment of a Na—Cs detector using different geometry anodes.

FIG. 3 illustrates an embodiment of a Na—Cs detector using different geometry anodes. In the detector 300, two ionization chambers 302, 304 are provided, again in series, in a flowing gas stream 306. In the embodiment shown, both ionization chambers 302, 304 are identical with the exception that the anode geometry is different. The first chamber 302 is provided with a coiled filament as the anode 302a and the second chamber 304 is provided with a straight filament as the anode 304a. The anodes 302a, 304a are heated by passing a steady current through the anode using current generators 302g, 304g and associated heating circuits (illustrated by a dashed line). In an alternative embodiment, the two anodes may be part of a single heating circuit as opposed to the independent circuits as shown. In an embodiment, the anode is heated to a temperature adequate to ionize the analytes. In the case of Cs and Na, a temperature above 800° C., such as 1000° C., is sufficient. Although FIG. 3 illustrates the coiled cathode chamber in series with the straight cathode chamber and being the first contacted by the flow of gas, in an alternative embodiment the straight cathode chamber could be placed before the coiled cathode chamber or the two chambers could be side-by-side in a parallel configuration, as discussed above, so that each chamber is only exposed to a portion of the gas flow.

The cathodes 302c, 304c may be any size or shape, such as a plate (as shown), a wire, a tube, a tube with the anode at its center, or a mesh that surrounds or partly surrounds their associated anode 302a, 304a. In an embodiment, the cathode is a metal tube with perforations that surround the associated anode. The perforations are sufficiently large to allow significant gas flow into the annular region to contact the anode. An example of this embodiment is discussed with reference to FIGS. 4 and 5 below.

A voltage potential is imposed across the anode-cathode pairs by a direct current voltage source 302v, 304v. Any voltage source may be used. In an embodiment, the anodes may be negatively charged and the cathode may be connected to ground or positively charge in order to create a target potential, V, between them.

In operation, metal vapor entering a detector through the perforation in the tubular will become ionized by the heat generated by a current applied to the anode. The ionization results in the separation of positively charged ions and negatively charged electrons. These charged particles drift toward the oppositely charged anode and cathode and result in the generation of an electrical current. The detected current is directly proportional to the number of ions created, and thus the concentration of Na and Cs in the gas.

The anode filament may be made of any suitable material that is conductive and that can withstand the heat and the gas environment and has a sufficient work function to ionize the Na and Cs. In an embodiment, the anode is selected from a noble metal or alloy thereof to provide superior corrosion resistance. For example, palladium, platinum, and alloys thereof are suitable anode materials. Rhenium, tantalum, and nickel-chromium alloys of steel may also be used.

In the embodiment shown, each chamber is provided with a current meter 302m, 304m to measure the current generated by the ionization of the analytes. The output of the current sensor is a signal, either analog or digital, that indicates the real time current through the cathode. The signals 312, 314 from the two chambers 302, 304 are passed to the processing system 308 where they are analyzed to determine the Na and Cs concentrations 310 in the gas.

In an embodiment, the Na and Cs concentrations are determined from the total current, $I_{tot}$, generated by each ionization chamber 302, 304 through an algorithm with an iterative process. In the algorithm, for example, the current is related to the element concentration using a power law calibration curve function:

$$C_x = a_x \cdot (I_x)^{b_x}$$

where:

$C_x$ is the element concentration;

$a_x$ and $b_x$ are parameters with respect to the element and the anode filament geometry determined through testing; and $I_x$ is the current generated by the element.

The calibration curve function (3) is generated for both Na and Cs elements, rearranged in the terms of $I_x$, and combined into the current output equations (1) and (2) that are described above. With knowing the total current, $I_1$ and $I_2$, generated by each ionization chamber 302, 304, output equation (2) may be substituted into output equation (1) such that it is reduced to a single variable, for example, Cs concentration. As such, the algorithm iteratively solves the output equation (1) for the Cs concentration. Then the calculated Cs concentration is inserted in the other output equation (2) to solve for the other variable, for example, Na concentration. In alternative embodiments, Na concentration may be iteratively solved for first and then Cs concentration is determined. Additionally, this algorithm may be used to determine any number of analytes using the same number of ionization chambers as described in FIG. 6 below.

Figure 4:
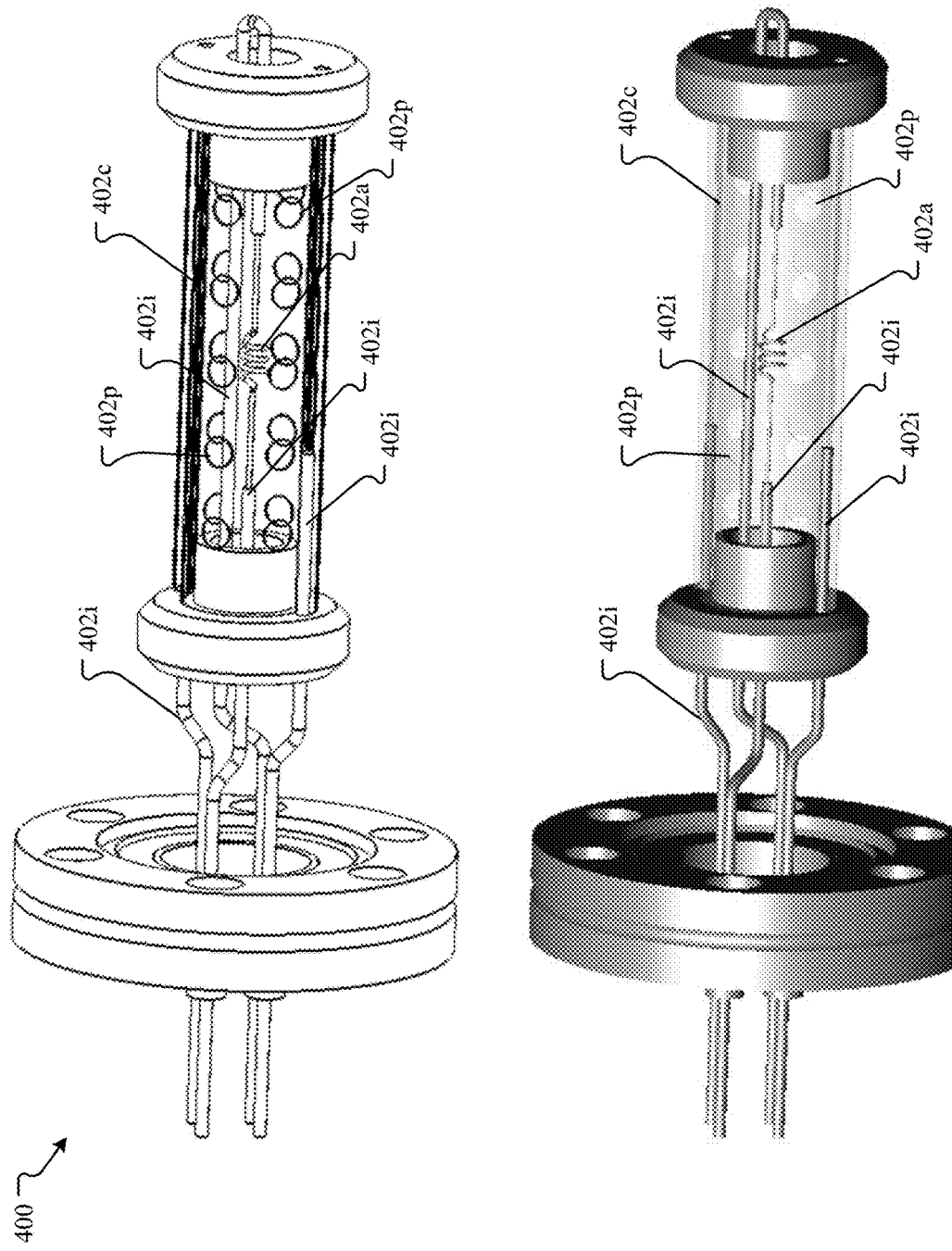
FIG. 4 illustrates several views of an embodiment of an ionization chamber using a coiled filament.

FIG. 4 illustrates several views of an embodiment 400 of an ionization chamber using a coiled filament. FIG. 4 includes a wireframe view and a shaded view showing the coiled filament anode 402a. The anode 402a is within a tubular cathode 402c provided with a number of circular openings in the side wall, referred to as perforations 402p to allow gas to enter the annular region and come in contact with the heat from the anode 402a. Insulation 402i is illustrated on portions of the anode and cathode wiring. This insulation 402i controls the location of the electrical field created between the anode 402a and cathode 402c as well as the location of the high temperature zone around the anode 402a.

Figure 5:
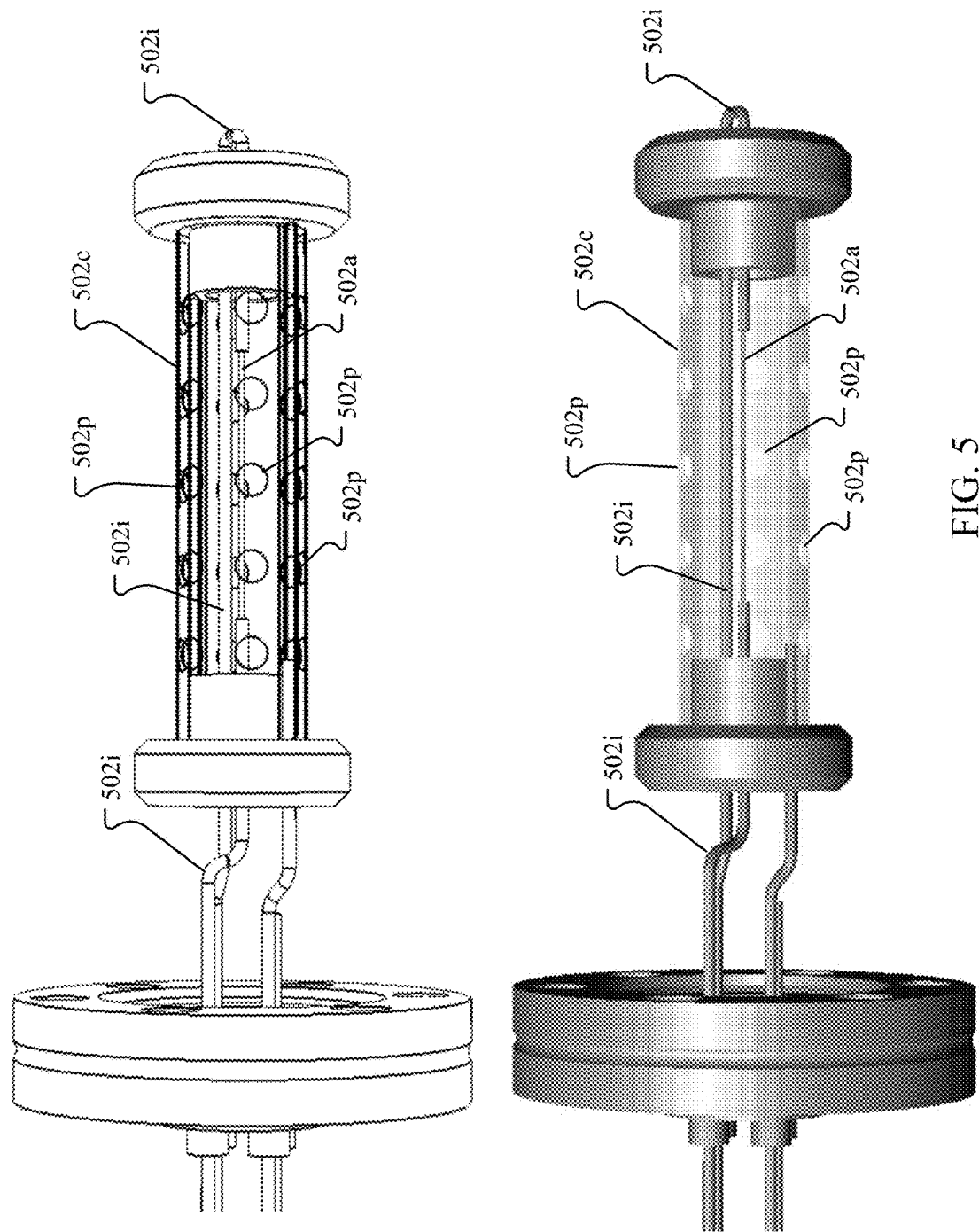
FIG. 5 illustrates several views of an embodiment of an ionization chamber that is the same as that of FIG. 4 except that it uses a straight filament.

FIG. 5 illustrates several views of an embodiment 500 of an ionization chamber that is the same as that of FIG. 4 except that it uses a straight filament. FIG. 5 includes a wireframe view and a shaded view showing the coiled filament anode 502*a*. The anode 502*a* is within a tubular cathode 502*c* provided with a number of circular openings in the side wall, referred to as perforations 502*p* to allow gas to enter the annular region and come in contact with the heat from the anode 502*a*. Insulation 502*i* is illustrated on portions of the anode and cathode wiring. This insulation 502*i* controls the location of the electrical field created between the anode 502*a* and cathode 502*c* as well as the location of the high temperature zone around the anode 502*a*.

Instead of a circular coil as shown in FIGS. 3 and 4, or a straight coil as shown in FIG. 5, any other geometries may be used, as long as the geometries, and thus the Cs and Na functions, of the two ionization chambers are different. For example, an elliptical coil (wire coiled around an elliptical cylinder), a square coil (wire coiled around a square prism), a triangular (wire coiled around a triangular prism) or other coil cross section may be used. Likewise, a 2-dimensional shape may be used for a filament, such as a sawtooth shape or a sinusoidal shape. In yet another variation, the number of coils or bends over a length of the anode may be varied. In yet another variation the diameter of the coils may be varied. In yet another embodiment, the anodes may be the same shape, but the potential across the anode and cathode, the coatings, or the anode and cathode materials may be different to achieve the different functions of the ionization chambers.

Figure 6:
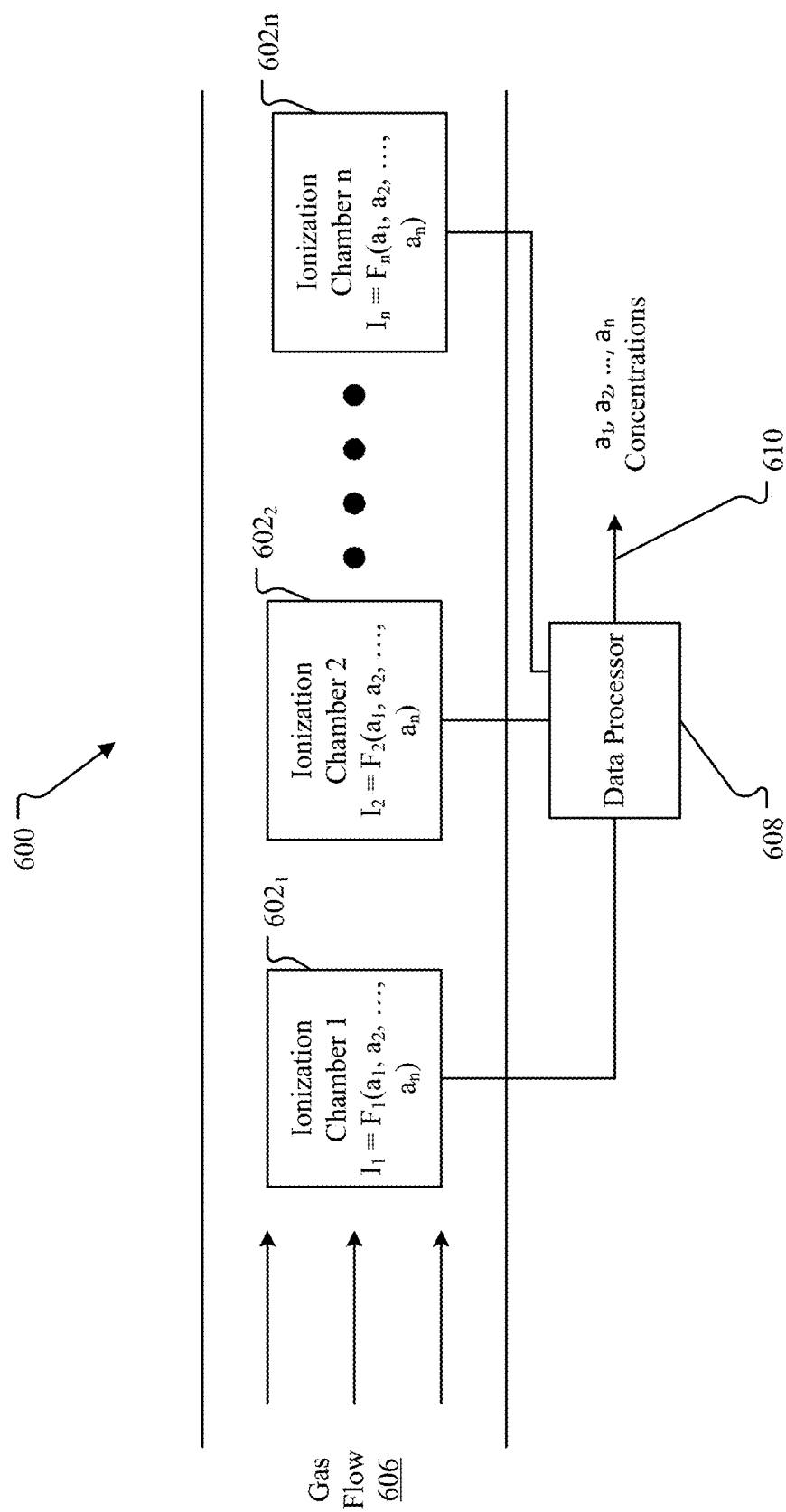
FIG. 6 illustrates another embodiment of an analyte detector that has some number (n) of three or more of ionization chambers that can be used to identify and differentiate n-number analytes.

FIG. 6 illustrates another embodiment of an analyte detector 600 that has some number (n) of three or more of ionization chambers that can be used to identify and differentiate n-number of analytes. In the embodiment shown, each ionization detector 602$_{1-n}$ has a different response function to the analytes allowing the effect of the different analytes in the gas flow 606 to be determined and the concentrations to be differentiated and reported 610 after analysis by the data processor 608.

In yet another embodiment, one or more of the ionization chambers may be used as a flow meter in addition to as an ionization chamber. In this embodiment, the temperature of the filament is maintained at a fixed temperature and the current is measured. In order to maintain the temperature in a changing flow of gas, the current must also change. By calibrating the ionization chamber with a carrier gas prior to use in a detector, the current response to variable flow may be determined. This allows one or more of the heating circuits of the ionization chambers to be used as a hot wire flow meter in addition to providing the ionization energy for ionizing the analytes. In situations, such as many of the applications described herein in which the carrier case is the vast majority of the gas, by weight, passing through the detector, the heating circuit need only be calibrated to determine its response to flow of pure carrier gas. For a more precise flow measurement, the current generated by the ionization may also be used to determine the flow, such as by subtracting the measured ionization current from the heating circuit current when determining flow.

Figure 7:
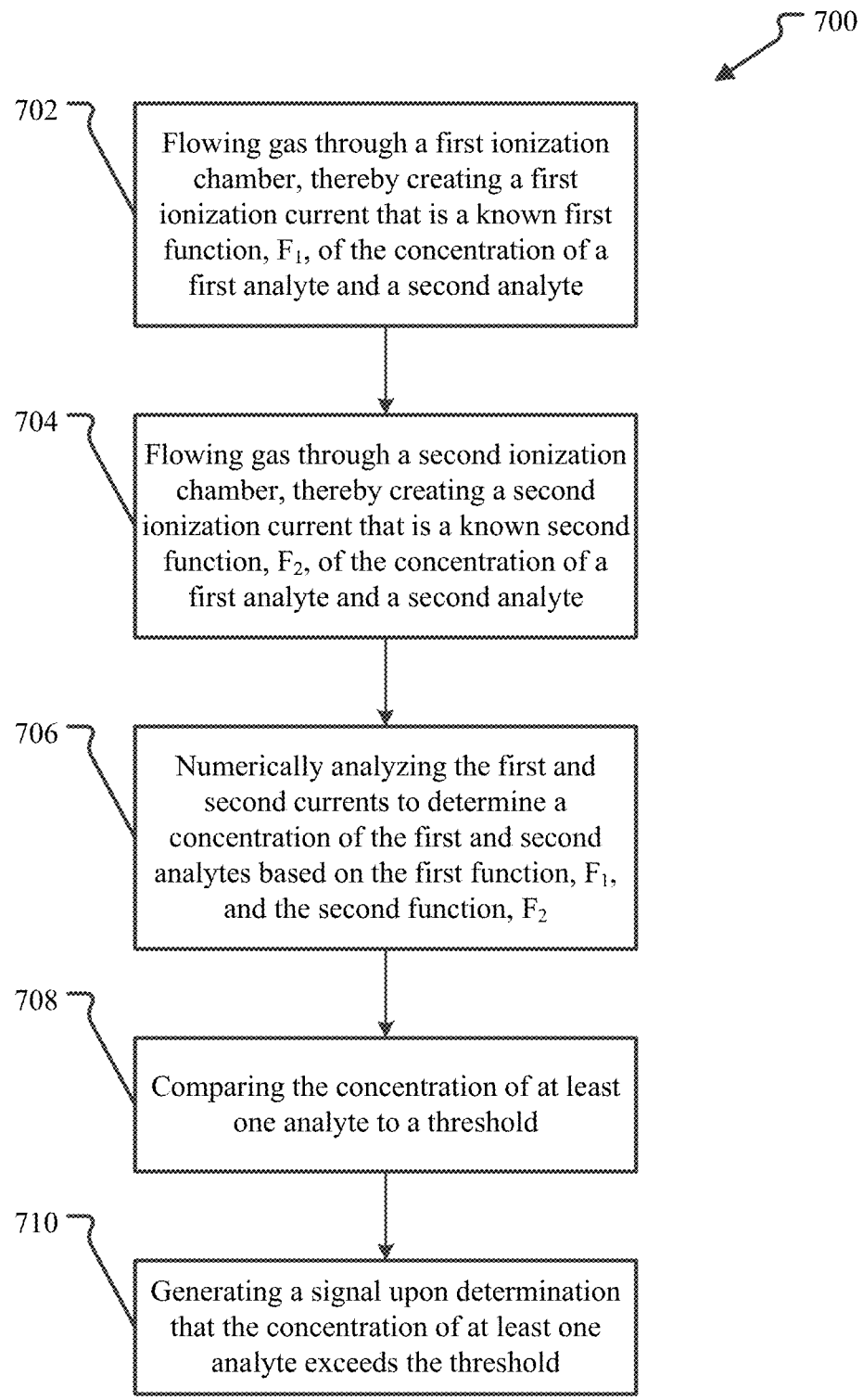
FIG. 7 illustrates an embodiment of a method for determining the concentration of two different analytes in a stream using ionization detectors as described above.

FIG. 7 illustrates an embodiment of a method for determining the concentration of two different analytes in a stream using ionization detectors as described above. In the embodiment shown, the method 700 begins by flowing gas through a first ionization chamber in a first gas monitoring operation 702. The first ionization chamber has been tested and has a known response function, $F_1$, that dictates the aggregated amount of current that will be generated between the anode and cathode of the chamber for given concentrations of the two analytes. Therefore, flowing the gas through the first chamber results in creating a first ionization current that is a known first function, $F_1$, of the concentration of a first analyte and a second analyte.

The method 700 further includes flowing gas through a second ionization chamber in a second gas monitoring operation 704. The second ionization chamber has been tested and has a known response function, $F_2$, that dictates the aggregated amount of current that will be generated between the anode and cathode of the chamber for given concentrations of the two analytes. The response function, $F_2$, is different than the response function, $F_1$, of the first ionization chamber. In an embodiment, this difference is due to a structural or material difference between the anodes or the cathodes of the two chambers. Therefore, flowing the gas through the second chamber results in creating a second ionization current that is a known second function, $F_2$, of the concentration of the first analyte and the second analyte.

The current outputs of the two chambers are then used in an analysis operation 706 to determine the concentration of the two analytes. The analysis operation 706 includes numerically analyzing the first and second currents, or signals derived from the currents such as an analog-to-digital conversion of the currents, to determine a concentration of the first and second analytes based on the first function, $F_1$, and the second function, $F_2$.

One or both of the concentrations may then be compared to one or more predetermined thresholds in a comparison operation 708. Each threshold may be associated with a different condition such as an acceptable range indicative of normal operation, a high range for which alarms should be generated, and an emergency range in which gas flow should be altered or terminated.

Based on the result of the comparison operation 708, a generation operation 710 generates one or more signals associated with an exceeded threshold or thresholds, such as a signal that the operation is normal, a signal that generates an alarm, and/or a signal that controls the flow of gas.

Notwithstanding the appended claims, the disclosure is also defined by the following clauses:

1. A detector comprising:
    a first ionization chamber having a first anode and a first cathode, the first anode having a first anode geometry; and
    a second ionization chamber having a second anode and a second cathode, the second anode having a second anode geometry different from the first anode geometry.
2. The detector of the above clause further comprising:
    a data processor that generates a concentration of a first analyte from a first output from the first ionization chamber and a second output from the second ionization chamber.
3. The detector of any one of the above clauses wherein the first output is one of a first current between the first anode and the first cathode or a signal derived from the first current.
4. The detector of any one of the above clauses wherein the first analyte is one of cesium and sodium.
5. The detector of any one of the above clauses wherein the cathode of at least one of the first ionization chamber and the second ionization chamber is a tubular cathode such that the anode is positioned within the tubular cathode.
6. The detector of any one of the above clauses wherein the tubular cathode has a sidewall with at least one opening defined therein.

7. The detector of any one of the above clauses wherein at least one of the cathode and anode have at least a portion of insulation.
8. The detector of any one of the above clauses wherein at least one of the first anode and the second anode is a noble metal or alloy thereof.
9. The detector of any one of the above clauses further comprising:
at least one third ionization chamber having a third anode and a third cathode, the third anode having a third anode geometry different from the first and second anode geometries.
10. The detector of any one of the above clauses wherein at least one of the first anode and the second anode is a coiled anode and the other anode is a straight anode.
11. A sodium-cesium detector comprising:
a first ionization chamber having a heated, coiled anode within a tubular cathode and outputting a first current proportional to sodium and cesium ions flowing through the first ionization chamber;
a second ionization chamber having a heated, straight anode within a tubular cathode and outputting a second current proportional to sodium and cesium ions flowing through the second ionization chamber; and
a data processor outputting a sodium concentration and a cesium concentration based on the first current and the second current.
12. The sodium-cesium detector of clause 11 wherein the first ionization chamber and the second ionization chamber are configured serially so that the sodium and cesium ions flow first through one of the two ionization chambers and then through the other.
13. The sodium-cesium detector of clause 11 wherein the first ionization chamber and the second ionization chamber are configured in parallel so that a first portion of the sodium and cesium ions flow through the first ionization chamber and a second portion sodium and cesium ions flow through the second ionization chamber.
14. A method of monitoring a gas for two analytes comprising:
flowing gas through a first ionization chamber, thereby creating a first ionization current that is a known first function, $F_1$, of the concentration of a first analyte and a second analyte;
flowing gas through a second ionization chamber, thereby creating a second ionization current that is a known second function, $F_2$, of the concentration of a first analyte and a second analyte;
analyzing the first and second currents to determine a concentration of the first and second analytes based on the first function, $F_1$, and the second function, $F_2$;
comparing the concentration of at least one analyte to a threshold; and
generating a signal upon determination that the concentration of at least one analyte exceeds the threshold.
15. The method of clause 14 wherein at least one of the first analyte and the second analyte is cesium and the other analyte is sodium.
16. The method of any one of clauses 14 and 15 wherein the first ionization chamber and the second ionization chamber are configured serially so that flowing gas through the first ionization chamber is before flowing gas through the second ionization chamber.
17. The method of any one of clauses 14-16 wherein the first ionization chamber and the second ionization chamber are configured in parallel so that flowing gas through the first ionization chamber is concurrent with flowing gas through the second ionization chamber.
18. The method of any one of clauses 14-17 wherein generating a signal further comprises generating an alarm.
19. The method of any one of clauses 14-18 wherein generating a signal further comprises controlling the flow of gas through the first and second ionization chambers.
20. The method of any one of clauses 14-19 wherein controlling the flow of gas further comprises stopping the flow of gas.
21. A sodium-cooled nuclear reactor comprising:
a reactor core;
a sodium coolant system;
a reactor control system; and
at least one sodium-cesium detector, each sodium-cesium detector having:
a first ionization chamber having a heated, coiled anode within a tubular cathode and outputting a first current proportional to sodium and cesium ions flowing through the first ionization chamber;
a second ionization chamber having a heated, straight anode within a tubular cathode and outputting a second current proportional to sodium and cesium ions flowing through the second ionization chamber; and
a data processor outputting to the reactor control system a sodium concentration and a cesium concentration determined based on the first current and the second current.

Notwithstanding that the numerical ranges and parameters setting forth the broad scope of the technology are approximations, the numerical values set forth in the specific examples are reported as precisely as possible. Any numerical value, however, inherently contains certain errors necessarily resulting from the standard deviation found in their respective testing measurements.

It will be clear that the systems and methods described herein are well adapted to attain the ends and advantages mentioned as well as those inherent therein. Those skilled in the art will recognize that the methods and systems within this specification may be implemented in many manners and as such is not to be limited by the foregoing exemplified embodiments and examples. In other words, functional elements being performed by a single or multiple components, in various combinations of hardware and software, and individual functions can be distributed among software applications at either the client or server level. In this regard, any number of the features of the different embodiments described herein may be combined into one single embodiment and alternate embodiments having fewer than or more than all of the features herein described are possible.

While various embodiments have been described for purposes of this disclosure, various changes and modifications may be made which are well within the scope contemplated by the present disclosure. For example, a multiple analyte detector may be designed to identify the concentration of Na, K and Cs for use with a reactor that uses a Na-K cooling salt. Numerous other changes may be made which will readily suggest themselves to those skilled in the art and which are encompassed in the spirit of the disclosure.

What is claimed is:
1. A detector comprising:
a first ionization chamber having a first anode and a first cathode, the first anode having a first anode geometry; and a second ionization chamber having a second anode and a second cathode, the second anode having a second anode geometry different from the first anode geometry.

2. The detector of claim 1 further comprising:
a data processor that generates a concentration of a first analyte from a first output from the first ionization chamber and a second output from the second ionization chamber.

3. The detector of claim 2 wherein the first output is one of a first current between the first anode and the first cathode or a signal derived from the first current.

4. The detector of claim 2 wherein the first analyte is one of cesium and sodium.

5. The detector of claim 1 wherein the cathode of at least one of the first ionization chamber and the second ionization chamber is a tubular cathode such that the anode is positioned within the tubular cathode.

6. The detector of claim 5 wherein the tubular cathode has a sidewall with at least one opening defined therein.

7. The detector of claim 5 wherein at least one of the cathode and anode have at least a portion of insulation.

8. The detector of claim 1 wherein at least one of the first anode and the second anode is a noble metal or alloy thereof.

9. The detector of claim 1 further comprising:
at least one third ionization chamber having a third anode and a third cathode, the third anode having a third anode geometry different from the first and second anode geometries.

10. The detector of claim 1 wherein at least one of the first anode and the second anode is a coiled anode and the other anode is a straight anode.

11. A sodium-cesium detector comprising:
a first ionization chamber having a heated, coiled anode within a tubular cathode and outputting a first current proportional to sodium and cesium ions flowing through the first ionization chamber;
a second ionization chamber having a heated, straight anode within a tubular cathode and outputting a second current proportional to sodium and cesium ions flowing through the second ionization chamber; and
a data processor outputting a sodium concentration and a cesium concentration based on the first current and the second current.

12. The sodium-cesium detector of claim 11 wherein the first ionization chamber and the second ionization chamber are configured serially so that the sodium and cesium ions flow first through one of the two ionization chambers and then through the other.

13. The sodium-cesium detector of claim 11 wherein the first ionization chamber and the second ionization chamber are configured in parallel so that a first portion of the sodium and cesium ions flow through the first ionization chamber and a second portion sodium and cesium ions flow through the second ionization chamber.

14. A method of monitoring a gas for two analytes comprising:

flowing gas through a first ionization chamber, thereby creating a first ionization current that is a known first function, $F_1$, of the concentration of a first analyte and a second analyte;
flowing gas through a second ionization chamber, thereby creating a second ionization current that is a known second function, $F_2$, of the concentration of a first analyte and a second analyte;
analyzing the first and second currents to determine a concentration of the first and second analytes based on the first function, $F_1$, and the second function, $F_2$;
comparing the concentration of at least one analyte to a threshold; and
generating a signal upon determination that the concentration of at least one analyte exceeds the threshold.

15. The method of claim 14 wherein at least one of the first analyte and the second analyte is cesium and the other analyte is sodium.

16. The method of claim 14 wherein the first ionization chamber and the second ionization chamber are configured serially so that flowing gas through the first ionization chamber is before flowing gas through the second ionization chamber.

17. The method of claim 14 wherein the first ionization chamber and the second ionization chamber are configured in parallel so that flowing gas through the first ionization chamber is concurrent with flowing gas through the second ionization chamber.

18. The method of claim 14 wherein generating a signal further comprises generating an alarm.

19. The method of claim 14 wherein generating a signal further comprises controlling the flow of gas through the first and second ionization chambers.

20. The method of claim 19 wherein controlling the flow of gas further comprises stopping the flow of gas.

21. A sodium-cooled nuclear reactor comprising:
a reactor core;
a sodium coolant system;
a reactor control system; and
at least one sodium-cesium detector, each sodium-cesium detector having:
a first ionization chamber having a heated, coiled anode within a tubular cathode and outputting a first current proportional to sodium and cesium ions flowing through the first ionization chamber;
a second ionization chamber having a heated, straight anode within a tubular cathode and outputting a second current proportional to sodium and cesium ions flowing through the second ionization chamber; and
a data processor outputting to the reactor control system a sodium concentration and a cesium concentration determined based on the first current and the second current.

* * * * *